(12) United States Patent
McKedy

(10) Patent No.: US 9,121,831 B2
(45) Date of Patent: Sep. 1, 2015

(54) COPPER, STARCH AND IODIDE MOISTURE INDICATOR

(75) Inventor: George E. McKedy, Williamsville, NY (US)

(73) Assignee: Multisorb Technologies, Inc., Buffalo, NY (US)

( * ) Notice: Subject to any disclaimer, the term of this patent is extended or adjusted under 35 U.S.C. 154(b) by 741 days.

(21) Appl. No.: 13/216,717

(22) Filed: Aug. 24, 2011

(65) Prior Publication Data

US 2013/0052740 A1 Feb. 28, 2013

(51) Int. Cl.
*G01N 33/18* (2006.01)
*G01N 21/81* (2006.01)

(52) U.S. Cl.
CPC ..................... *G01N 21/81* (2013.01)

(58) Field of Classification Search
USPC .................................. 436/41, 166
See application file for complete search history.

(56) References Cited

U.S. PATENT DOCUMENTS

| | | | | |
|---|---|---|---|---|
| 2,460,067 | A * | 1/1949 | Davis | 436/41 |
| 2,460,072 | A * | 1/1949 | Davis | 436/41 |
| 3,266,868 | A | 8/1966 | Harvil | |
| 3,632,364 | A * | 1/1972 | Thomas et al. | 428/29 |
| 3,788,863 | A * | 1/1974 | Scheuer | 106/31.32 |
| 3,888,739 | A | 6/1975 | Whetzel et al. | |
| 4,525,214 | A | 6/1985 | Panken | |
| 5,286,061 | A * | 2/1994 | Behm | 283/95 |
| 6,655,315 | B1 | 12/2003 | Gattiglia | |
| 7,163,909 | B2 | 1/2007 | Ukpabi | |
| 7,648,842 | B2 | 1/2010 | Hartlep | |
| 2004/0051081 | A1 | 3/2004 | Moreton | |
| 2008/0248948 | A1 * | 10/2008 | Hartlep | 503/201 |
| 2009/0047176 | A1 | 2/2009 | Cregger | |
| 2010/0252779 | A1 | 10/2010 | McKedy | |

OTHER PUBLICATIONS

PCT—Notification of Transmittal of the International Search Report and the Written Opinion of the International Searching Authority, or the Declaration; dated Dec. 17, 2012 in corresponding PCT International Application No. PCT/US2012/052015 (2 pages).
PCT—International Search Report dated Dec. 17, 2012 in corresponding PCT International Application No. PCT/US2012/052015 (3 pages).
PCT—Written Opinion of the International Searching Authority dated Dec. 17, 2012 in corresponding PCT International Application No. PCT/US2012/052015 (5 pages).
A Good Company website http://agoodco.org/ 1 page; dated Apr. 8, 2010.
IOPHARDT: Virtual Chembook (http://www.elmhurst.edu/~chm/vchembook/548starchiodine.html) 2 pages; dated Apr. 8, 2010.
OPHARDT: Virtual Chembook (http://www.elmhurst.edu/~chm/vchembook/547starch.html) 2 pages; dated May 5, 2010.
Amylopectin—Wikipedia http://en.wikipedia.org/wiki/Amylopectin 1 page; dated May 5, 2010.

* cited by examiner

*Primary Examiner* — Arlen Soderquist
(74) *Attorney, Agent, or Firm* — Lee & Hayes, PLLC

(57) ABSTRACT

The invention relates to a moisture indicator which includes iodide, copper, and starch.

9 Claims, No Drawings

COPPER, STARCH AND IODIDE MOISTURE INDICATOR

BACKGROUND OF THE INVENTION

1. Field of the Invention

The present invention relates to humidity indicators used for indicating the relative humidity in an environment, and more particularly, to copper humidity indicators which change color at different relative humidities in an environment.

2. Description of Related Art

A variety of humidity indicators exist today. One type of humidity indicator is a humidity indicating card, which is used for many purposes including, determining the relative humidity in shipping containers and packages, such as packaged electronics and telecommunication products. The humidity indicator cards are typically impregnated with a humidity sensitive composition and dried. Most humidity indicating cards made today use cobalt chloride as the indicator, which changes color based on the level of hydration of the cobalt chloride. Cobalt chloride can change from a blue color, when it has one water of hydration, to a pink color when it has six waters of hydration. That is, the blue color becomes increasingly red with each additional water of hydration. Therefore, one can determine the approximate humidity based on the color present on the card. An array of humidity indication areas can be included on the card, wherein increasing humidity levels are required to change different areas of indication on the card from blue to pink.

A problem with humidity indicators using cobalt chloride is that the cobalt chloride is a known irritant and a toxin. Further, the use of cobalt chloride is subject to regulation when used with food and pharmaceutical products. Thus, cobalt chloride humidity indicators have limited applications and are not useful in the food and pharmaceutical industries.

Some types of humidity indicator cards have impregnated halides or other salts capable of releasing $Cu^{2+}$ ions. International Publication No. WO 02/44712 discloses a humidity indicator paper impregnated with copper salts, a synergistic salt, and a dye.

Other types of humidity indicators include the use of humidity indicating gels. In US Patent Application Publication No. 2004/0051081 Moreton discloses a silica gel material impregnated with copper and bromide to provide a relative humidity indicator. U.S. Pat. No. 6,655,315 Gattiglia discloses a silica gel impregnated with copper chloride and hygroscopic salts, wherein the silica gel changes color to indicate the presence of moisture.

There remains a need for an improved humidity indicator that provides easily detectible color changes and that is non-toxic.

BRIEF SUMMARY OF THE INVENTION

The present invention includes a moisture indicator comprising iodide, copper, and starch

DETAILED DESCRIPTION OF THE INVENTION

This invention overcomes disadvantages of prior practices. The present invention provides a non-toxic humidity indicator. The invention also provides a device that can be used in food and pharmaceutical product packages. Further, the invention provides a device that indicates when a desiccant needs to be changed. The invention also provides a color change in a capsule or sachet that is easily detectable by a user. Further, the invention allows one to vary the color of the indicator areas. These and other advantages will be apparent from the detailed description below.

The present invention includes a humidity indicating device that comprises the invention moisture indicator in a water vapor permeable container that has at least one area of the package that is generally transparent, such that the human eye can easily see the color change. The package may be a capsule. The package in a preferred form is a sachet that is formed in least in part of a water vapor transmitting material such water vapor permeable, but water impermeable, nonwoven fabrics of polyethylene such as Tyvek®. A water vapor permeable fabric or film that is transparent may be formed of polyethylene or polyester film or polyethylene fabric. If needed, the envelope is provided with a transparent film window that may or may not be water vapor permeable. If a capsule is used, it may be transparent and may be, if needed, provided with a gas permeable area of polymer or fabric. The gas permeable area may be a micro porous polymer sheet or fabric, such as Gore-Tex fabric. A water vapor permeable capsule may be formed of hydroxyl propyl methyl cellulose or other cellulose based materials that could be used.

The color change indicators of the invention change color at between 20 and 25% relative humidity. The water absorbent typically is able to absorb enough water to reach a higher relative humidity in the sachet or capsule. Therefore, the color change is a warning that water vapor absorption has ceased or is close to ceasing. The humidity indicating composition includes copper, an iodide salt, and a starch in effective combinations that will react with water vapor at a certain humidity to provide color change.

When starch, comprising an amylose starch is blended with iodine in water a starch/iodine complex is formed which produces an intense blue color. It seems that the form of $I^{-5}$ ions get stuck in the coils of the beta amylose starch molecules. The starch forces the iodine atoms into a linear arrangement in the central groove of the amylose coil. There is some transfer of charge between the starch and the iodine. That changes the way the electrons are confined and so changes the energy levels. The iodine starch complex has the energy level spacings that are just so for absorbing the visible light giving the complex its intense blue color. When using copper II sulfate pentahydrate and potassium iodine instead of pure iodide with the amylose starch and depositing this on the silica gel, we can get a silica gel that is white when dry and blue when wet. When the silica gel is dry a copper (II) sulphate iodide complex is formed which does not form a blue color with the starch. When the silica gel is wet this iodide complex converts to an iodide ion that can then get into the linear arrangement in the central groove of the amylose starch coil producing the blue color.

The amylose starch may be present in any suitable amount in the moisture indicator of the invention. Typical amounts of amylose starch would be between 0.01 and 29 percent by weight. A suitable range generally would be between 0.01 and 15 percent by weight. A preferred amount would be between 0.1 and 2.9 percent by weight for good color and moisture sensitivity.

Starch can be separated into the two fractions amylose and amylopectin. The structure of the amylose consists of lone polymer chains of glucose units connected by an alpha acetyl linkage. As a result of the bonds angles in the alpha acetyl linkage, amylose actually forms a spiral much like a coiled spring. Amylose in starch is responsible for the formation of a deep blue color in the presence of iodine. The iodine molecule slips inside the amylose coil. The iodine is not very soluble in water so the potassium iodine is dissolved in water with the copper (II) sulfate pentahydrate. This makes a complex in the water that is more soluble in water. If starch amylose is not present the blue color will not appear. Starch amylopectin does not give the color nor does cellulose or disaccharides such as sucrose or sugar. A starch that is a mixture of amylose and amylopectin types is operable in the invention, but only the amylose starch is active to give the blue color. Only the iodine element in the presence of the iodide ion will give the blue color with the amylose starch. Neither iodine element alone nor the iodide ions alone will give the blue color.

Any suitable metallic compound can be utilized in the instant invention. The preferred metallic material is a copper salt material or other soluble copper compound. Typical of such materials are copper sulfates. A most preferred material is copper sulfur pentahydrate as it produces a bright blue and provides color change as it is dried to low humidity.

Any suitable amount of copper material may be utilized. Typically, the copper material is present in an amount of between 0.0004 and 4 percent by weight. The preferred copper material may suitably be present in an amount of between 0.01 and 1 percent of the moisture indicator. The preferred Copper II sulfate pentahydrate is most preferably present in the moisture indicator in an amount between 0.04 and 0.4 percent by weight for good moisture sensitivity and color change.

The material typically is provided with a carrier material for the copper sulfate, starch and iodide active materials. Any hydrophilic material may be suitable in the invention. Typical of such materials are cellulose fibers and methyl cellulose superabsorbents. A preferred material is silica gel as it is a water absorbent, it is low in cost, and does not react with the materials utilized in the color forming process.

The carrier material may be present in the moisture indicator in any suitable amount. Typically it would be present in an amount of between 65 and about 99.9 percent by weight. A suitable amount would be between 83 and 99.9 percent by weight. A preferred amount for silica gel is 96.5 to 98 percent by weight for fast water absorption and compatibility with the copper and iodide compounds.

The iodide ion source for the invention may be from any suitable material that will dissolve in water and not interfere with the reaction of the iodide in starch. The iodide may be formed by dissolving any of the ordinary halide salts such as sodium iodide, lithium iodide, or iodide complexes. A preferred salt is potassium iodide as it is rapidly soluble and compatible with the sulfate and starch.

The halide iodide salt in the moisture indicator is typically present in an amount of between 0.01 and 3 percent by weight of the moisture indicator. A suitable amount of iodide salt would be between 0.05 and 1 percent by weight. For the most preferred potassium iodide salt, an amount between 0.01 and 3 percent is preferred for good moisture sensitivity and color change.

The halide iodide salt is typically present in an amount of between 0.01 and 3 percent by weight of the moisture indication. A suitable amount of iodide salt would be between 0.05 and 1 percent by weight. For the most preferred potassium iodide salt an amount between 0.01 and 3 percent is preferred for good moisture sensitivity and color change.

The following examples are illustrative and not exhaustive of the invention. Parts and percentages are by weight unless otherwise indicated.

Example 1

The following formulation mixture was made:
300. grams of silica gel
120. grams of 5% solution of National Starch 1215 amylose starch in water
120. grams of water containing 0.1% (0.12 grams) copper (II) sulphate pentahydrate and 0.3% (0.36 grams) potassium iodide.

The two solutions were made and then each was mixed together with the silica gel. The silica gel was allowed to adsorb the solutions for about 2 hours. Then the mixture was dried overnight at 110° C. The next morning when the silica gel was dry the silica gel was white in color. When this silica gel was humidified the color was blue.

Example 2

The following formulation mixture was made:
To 30 grams of water, with mixing to dissolve, is added 0.03 grams of copper II sulfate pentahydrate and 0.09 grams of sodium iodide. To this solution is added, with mixing 30 grams of 5% solution of National Starch 1215, an amylose starch. Then 75 grams of silica gel is mixed into the solution. The mixture is then dried at about 120° C. The dry material was very dark blue when made, brown/blue when dried, and purple when wetted by absorption at about 30% humidity.

In Examples 3-8 the forming process of Example 2 was repeated.

Example 3

Control

The following formulation mixture was made:
75 grams silica gel
30 grams of 5% solution of National Starch 1215 in water
30 grams of water containing 0.03 grams of copper sulfate pentahydrate and 0.006 grams of sodium iodide The mixture is then dried at about 110° C. The dry material was a nice blue when made, white when dried, and white again when water was added. The material is believed to need more sodium iodide to change color when wet.

Example 4

The following formulation mixture was made:
75 grams silica gel
30 grams of 5% solution of National Starch 1215 in water
30 grams of water containing 0.012 grams of sodium iodide The mixture is then dried at about 110° C. The dry material is a nice blue color when wet, it is light purple when dried and bright purple when wetted again.

Example 5

Control

The following formulation mixture was made:
75 grams silica gel
30 grams of 5% solution of National Starch 1215 in water
30 grams of water containing 0.07 grams of potassium iodide The mixture is then dried at about 110° C. The dry material was white in color when made and no color change after. The material is believed to need more potassium iodide to change color when wet.

Example 6

The following formulation mixture was made:
75 grams silica gel
30 grams of 5% solution of National Starch 1215 in water
30 grams of water containing 0.13 grams of potassium iodide The mixture is then dried at about 110° C. The dry material was a slight purple color when made, a yellow color when dried, and a nice purple color when wet again.

Example 7

The following formulation mixture was made:
75 grams silica gel
30 grams of 5% solution of National Starch 1215 in water
30 grams of water containing 0.03 grams of sodium iodide The mixture is then dried at about 110° C. The dry material was a slight purple color when made, white after being dried, and light purple again when wetted.

Example 8

Control

The following formulation mixture was made:
75 grams silica gel
30 grams of 5% solution of National Starch 1215 in water
30 grams of ethyl alcohol containing 0.04 grams of sodium iodide The mixture is then dried at about 110° C. The dry material is white and does not change color when wet. It is believed that more sodium iodide is needed to work with the ethyl alcohol.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A humidity indicator comprising:
a water vapor permeable container; and
iodide disposed in the water vapor permeable container;
copper disposed in the water vapor permeable container; and
starch disposed in the water vapor permeable container.

2. The humidity indicator of claim 1, wherein the water vapor permeable container comprises a capsule.

3. The humidity indicator of claim 1, wherein the water vapor permeable container comprises a transparent section for viewing the contents of the water vapor permeable container.

4. The humidity indicator of claim 3, wherein the starch comprises amylose starch.

5. The humidity indicator of claim 1, wherein the water vapor permeable container is impermeable to liquid water.

6. The humidity indicator of claim 1, further comprising a carrier material.

7. The humidity indicator of claim 6, wherein the carrier material comprises a hydrophilic material.

8. The humidity indicator of claim 6, wherein the carrier material comprises at least one of cellulose fiber, methyl cellulose superabsorbents, or silica gel.

9. The humidity indicator of claim 1, wherein the contents of the water vapor permeable container change color at between about 20% and about 25% relative humidity.

* * * * *